United States Patent [19]
Portnoy et al.

[11] Patent Number: 4,786,445
[45] Date of Patent: Nov. 22, 1988

[54] METHOD OF ATTACHING A FIXATION MEMBER TO AN INTRAOCULAR LENS

[75] Inventors: Vladimir Portnoy, Irvine; Albert C. Ting, Niguel, both of Calif.

[73] Assignee: Allergan, Inc., Irvine, Calif.

[21] Appl. No.: 5,934

[22] Filed: Jan. 22, 1987

Related U.S. Application Data

[62] Division of Ser. No. 754,417, Jul. 11, 1985, abandoned.

[51] Int. Cl.[4] ............................................. B29D 11/00
[52] U.S. Cl. ...................... 264/1.4; 264/1.7; 264/25; 623/6
[58] Field of Search ............ 264/1.4, 1.7, 25; 623/6

[56] References Cited

U.S. PATENT DOCUMENTS

| | | | |
|---|---|---|---|
| 4,025,965 | 5/1977 | Siegmund. | |
| 4,104,339 | 8/1978 | Fetz et al. | 264/249 |
| 4,150,471 | 4/1979 | Richards et al. | 264/249 |
| 4,307,043 | 12/1981 | Chase et al. | 264/1.4 |
| 4,510,005 | 4/1985 | Nijman | 264/1.4 |

Primary Examiner—James Lowe
Attorney, Agent, or Firm—Gordon L. Peterson

[57] ABSTRACT

A method of attaching a fixation member to an optic comprising providing the optic with a cavity opening adjacent the peripheral edge of the optic with a shoulder in the cavity, inserting an inner end portion of the fixation member into the cavity, transmitting laser energy through the optic to the inner end portion of the fixation member to cause the inner end portion to become flowable, and allowing the flowable portion of the fixation member to harden and interlock with the shoulder to resist withdrawal of the fixation member from the cavity.

11 Claims, 2 Drawing Sheets

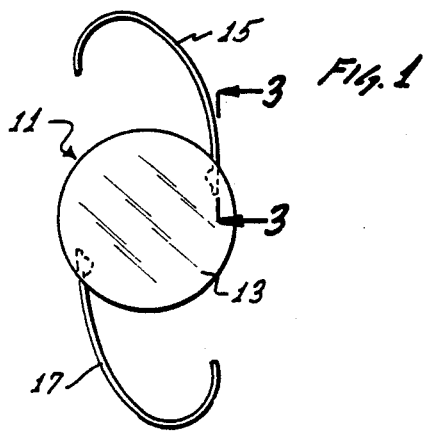
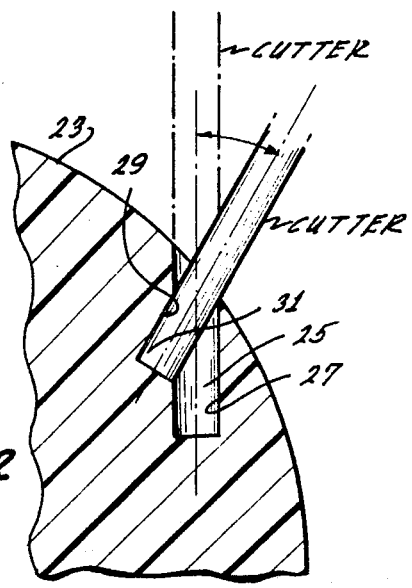
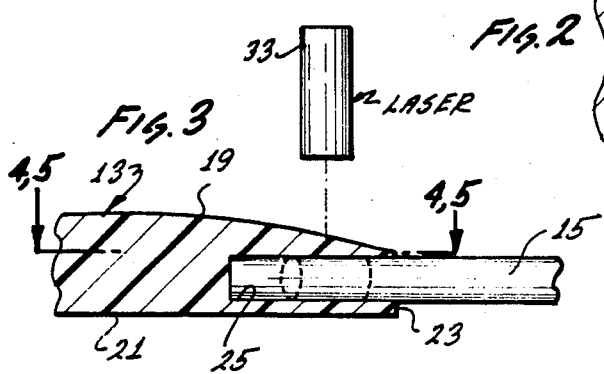
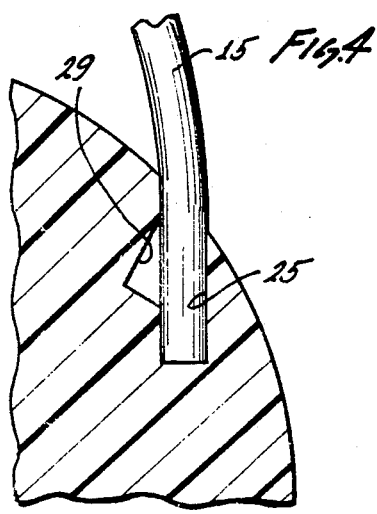
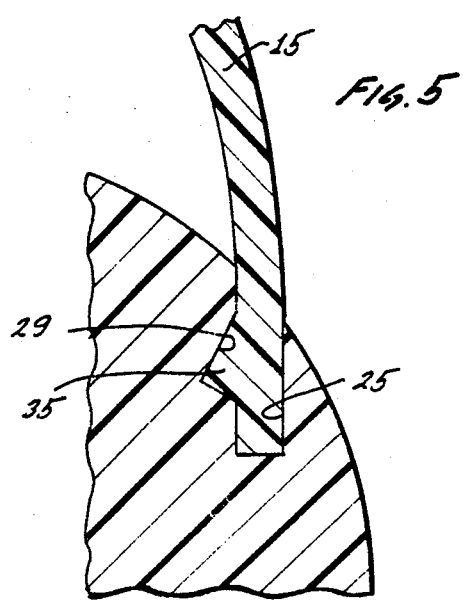

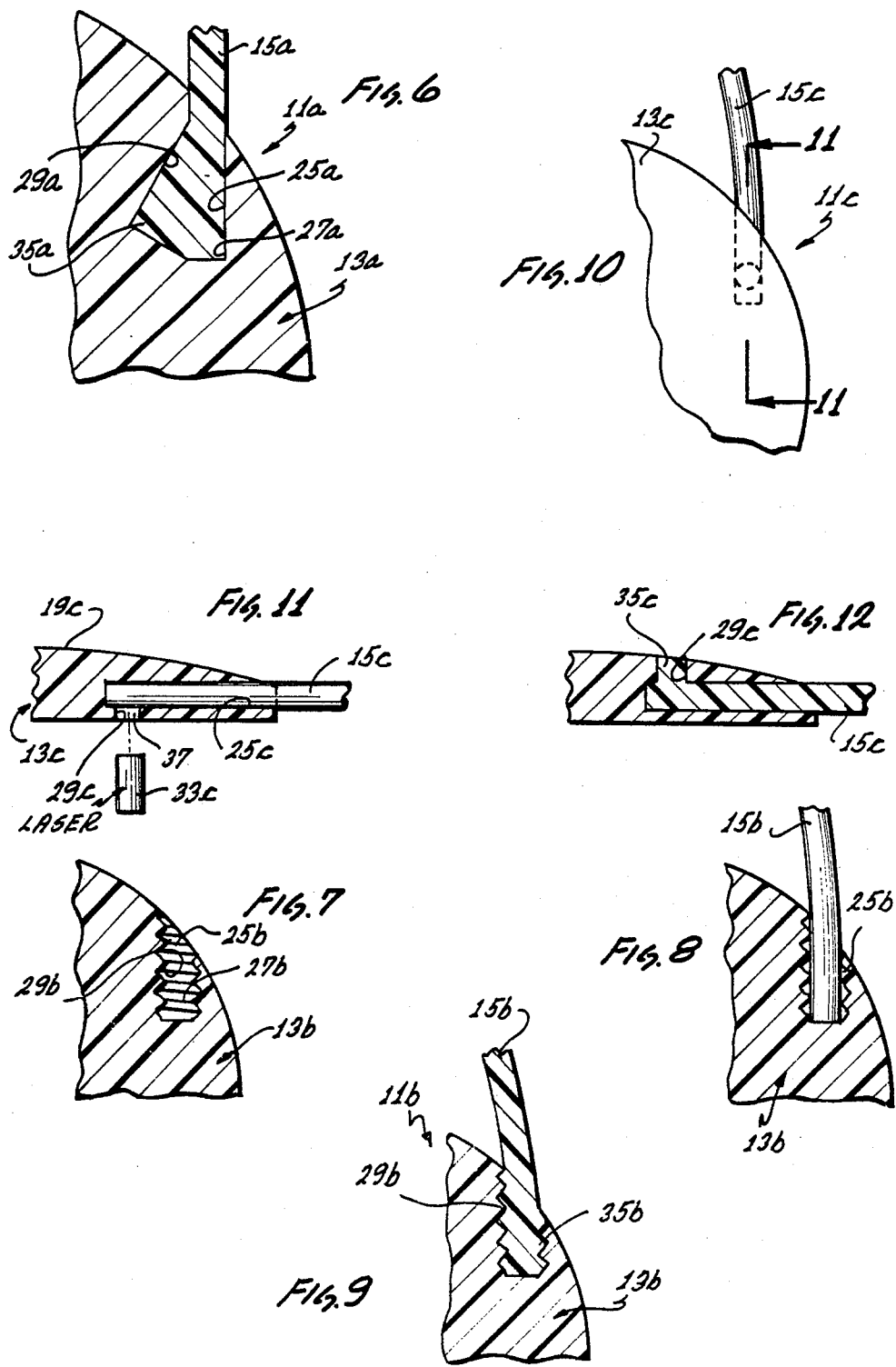

METHOD OF ATTACHING A FIXATION MEMBER TO AN INTRAOCULAR LENS

This application is a division, of application Ser. No. 754,417, filed July 11, 1985, now abandoned.

BACKGROUND OF THE INVENTION

An intraocular lens (IOL) of the type used for replacement of the natural lens of the human eye typically comprises an optic and one or more fixation members. When implanted, the optic serves as the lens of the eye, and the fixation members are used to mount or fix the optic in position within the eye.

The optic typically has anterior and posterior faces, at least one of which may be curved, and a peripheral edge, which is often cylindrical. The optic may be formed of various different materials, including polymethylmethacrylate (PMMA).

The fixation members are typically resilient, and they are attached to the optic. In some IOL's, the fixation members are formed integrally with the optic. However, in many other IOL's, the fixation members are separate members which must be attached to the optic.

One common method of attachment is to drill intersecting holes into the periphery of the optic and insert and inner end portion of the fixation member into one of the holes. A heated probe is then inserted through the other of the holes and into contact with the inner end portion of the fixation member to melt it. This causes the inner end portion of the fixation member to flow into the second hole and harden to thereby provide a mechanical interlock with the optic. This technique requires a skilled technician and is not as fast as desired in that it requires the drilling of two precision, very small diameter holes into the optic and the subsequent insertion of a very fine heated probe into one of the small-diameter holes. In addition, there is the danger that the optic will be damaged by the hot probe or from the clean-up work done on the optic following use of the hot probe.

It is also known, as shown in Chase et al U.S. Pat. No. 4,307,043, to provide a threaded bore extending between the faces of the optic and to insert the fixation member completely through the optic so that both ends of the fixation member project beyond the optic. A tool applies heat to one end of the fixation member to cause the end of the fixation member to fill the bore to attach the fixation member to the optic. This technique, although satisfactory for some applications, has the disadvantage of requiring contact between a heat-applying member and one end of the fixation member. This contact must be carried out with skill and accuracy to avoid damaging the optic.

SUMMARY OF THE INVENTION

This invention solves these problems by providing a method of attaching a fixation member to the optic which does not require contacting of the fixation member with a heat-applying member. As a result, IOL assembly is accomplished more rapidly, the risk of damage to the optic during the attaching process is reduced and the attachment process can be carried out by relatively unskilled personnel. In addition, the attachment method of this invention can be carried out with a minimum number of bores being formed in the optic.

To carry out the method of this invention, an inner end portion of a fixation member is inserted into an outwardly opening cavity of the optic. Laser energy is then transmitted through the optic to the inner end portion of the fixation member. The laser energy is absorbed in the inner end portion of the fixation member sufficiently to heat the inner end portion to cause at least some of the inner end portion to flow. In this manner, contact of the fixation member with a separate heating member is eliminated.

With this invention, the material of the optic is preferably not heated sufficiently to cause any significant flow of the optic material. Accordingly, if an error is made and the laser energy is poorly aimed, the optic is not ruined as it would be if a similar error were made with a heating member.

The cavity can extend inwardly from either face of the optic or from the peripheral edge. Preferably, the cavity is in the form of a bore which extends inwardly from adjacent the peripheral edge of the optic generally in the plane of the optic.

In order to obtain a strong attachment between the fixation member and the optic, the cavity has a shoulder in it, and the heated material of the fixation member flows behind the shoulder. Accordingly, when the flowable portion of the fixation hardens, it interlocks with the shoulder to form a strong mechanical lock which resists withdrawal of the fixation member from the cavity. In addition, by appropriately constructing the shoulder, this interlock can also strongly interlock the fixation member and optic against relative rotation. Thus, the primary attachment between the fixation member and the optic is a mechanical interlock rather than the bonding of the surfaces of these two members together.

As used herein, shoulder means any irregularity which can mechanically interlock with the fixation member. For example, the shoulder preferably has a dimension of at least about 0.002 inch radially of the cavity.

The laser energy can be transmitted through the optic in different ways. For example, the laser energy can be transmitted directly through the material of the optic to the fixation member. When this technique is used, the laser energy transmission characteristics of the optic and the inner end portion of the fixation member at the wavelengths of interest must be sufficiently different so that the laser energy is transmitted by the optic without melting the optic and absorbed by the inner end portion of the fixation member sufficiently to cause flow. For example, this can be brought about by using different materials for the optic and fixation member and with a PMMA optic and a polypropylene fixation member, laser energy in the near infrared band of, for example, from about 1.06 to about 1.3 microns wavelength can be used.

Another approach is to drill, or otherwise form, a second bore which extends from the exterior of the optic and which intersects the bore in which the inner end portion of the fixation member is positioned and directing the laser energy through this second bore. When this is done, the second bore can form the shoulder into which the flowable material of the fixation member flows to form the interlock. This technique does not require that the laser energy be of a wavelength which would not be substantially absorbed by the optic; however, it is preferred in this event also to utilize laser energy that would not be absorbed by the optic sufficiently to cause the optic to flow in that this provides a desirable tolerance for error in aiming of the laser beam.

The shoulder can be formed in any way which will provide the desired interlock. For example, the peripheral wall of the cavity or bore into which the inner end portion of the fixation member is inserted can be drilled or milled to provide the shoulder. Alternatively, the peripheral wall of the cavity can be grooved, and such grooves can be, for example, screw threads.

An IOL made in accordance with the method of this invention has the fixation members securely mechanically attached to the optic. In addition, it is possible to provide an IOL which has no supplementary bores or cavities leading to the cavity which contains the inner end portion of the fixation member. Such an IOL would include an optic with a blind cavity opening adjacent the periphery of the optic, a shoulder in the cavity and a fixation member having an inner end portion received in the cavity and formed in situ into a configuration to mechanically interlock with the shoulder to attach the fixation member to the optic.

The invention, together with additional features and advantages thereof, may best be understood by reference to the following description taken in connection with the accompanying illustrative drawing.

BRIEF DESCRIPTION OF THE DRAWING

FIG. 1 is an elevational view of an IOL constructed in accordance with the teachings of this invention.

FIG. 2 is an enlarged fragmentary sectional view showing one manner in which the cavity for receiving the inner end portion of the fixation member can be formed.

FIG. 3 is an enlarged fragmentary sectional view taken generally along line 3—3 of FIG. 1 illustrating the use of a laser to attach the fixation member to the optic.

FIGS. 4 and 5 are fragmentary sectional views similar to FIG. 2 illustrating the fixation member before and after it has been heated by the laser, respectively.

FIG. 6 is a fragmentary, sectional view similar to FIG. 5 showing an alternate form of shoulder.

FIG. 7 is a fragmentary, sectional view similar to FIG. 2 illustrating the use of screw threads for the shoulder.

FIGS. 8 and 9 are fragmentary, sectional views similar to FIG. 7 showing the fixation member before and after its attachment to the optic, respectively.

FIG. 10 is a fragmentary plan view showing another embodiment of the invention.

FIG. 11 is a sectional view taken along line 11—11 of FIG. 10 illustrating the use of the laser to heat the fixation member.

FIG. 12 is a sectional view similar to FIG. 11 after the laser has been used to attach the fixation member to the optic.

DESCRIPTION OF THE PREFERRED EMBODIMENTS

FIG. 1 shows an IOL 11 of the type which can be implanted in the human eye. The IOL 11 includes an optic 13 and identical fixation members 15 and 17. The fixation members 15 and 17 may be of any desired configuration, and the J-shaped configuration is purely illustrative. Similarly, the optic 13 may be of any desired shape, and the circular shape illustrated is also purely illustrative.

The optic 13 has an anterior face 19 (FIG. 3), a posterior face 21 and a peripheral edge 23. In the embodiment illustrated, the faces 19 and 21 are convex and planar, respectively, and the peripheral edge is cylindrical.

The fixation members 15 and 17 are separate members which are attached to a peripheral region of the optic 13. Except for the means and method of attaching the fixation members 15 and 17 to the optic 13, the IOL 11 may be of conventional construction.

To attach the fixation member 15 to the optic 13, the optic 13 has a cavity in the form of a cylindrical bore 25 (FIG. 2) drilled into it from the peripheral edge 23. The bore 25, which lies generally in the plane of the optic as shown in FIG. 3, has a peripheral wall 27 and may have, for example, a diameter of about 0.006 inch. A sloping peripheral shoulder 29 is formed in the peripheral wall. Although the shoulder 29 can be formed in different ways, in the embodiment of FIGS. 1-5, it is formed by drilling a separate bore 31 into the peripheral wall 27 of the bore 25. The bore 25 is a blind bore in that it opens only at one location, which in this embodiment is at the peripheral edge 23.

An inner end portion of the fixation member 15 is then inserted into the bore 25 until it strikes the end of the bore as shown in FIGS. 3 and 4. The laser energy from a laser 33 is then transmitted through the material of the optic 13 to the inner end portion of the fixation member 15. The laser energy is absorbed by the inner end portion of the fixation member 15 sufficiently to heat the inner end portion to cause at least some of the inner end portion to flow behind the shoulder 29 and fill the bore 31 as shown in FIG. 5. The flowable portion of the fixation member 15 is then allowed to cool to form a projection 35 which mechanically interlocks with the shoulder 29 to resist withdrawal from the bore 25. The interlock between the shoulder 29 and the projection 35 will also resist relative rotation of the optic 13 relative to the fixation member 15.

The optic 13 is constructed of a material which will transmit the laser energy from the laser 33 without absorbing sufficient laser energy to melt any significant part of the optic. Conversely, the fixation member 15 is constructed of a material which will absorb sufficient laser energy transmitted through the optic 13 so as to form the projection 35. In this embodiment, the optic 13 is constructed of PMMA, and the fixation members 15 and 17 are constructed of polypropylene. Although various lasers could be used, the laser 33 is a Nd:YAG laser which provides laser energy at a wavelength of 1.06 microns.

The fixation member 17 may be attached to the optic 13 in the same manner as the fixation member 15. Additional fixation members may be attached to the optic 13 in the same manner, if desired.

FIG. 6 shows an IOL 11a which is identical to the IOL 11 in all respects not shown or described herein. Portions of the IOL 11a corresponding to portions of the IOL 11 are designated by corresponding reference numerals followed by the letter "a." The primary difference between the IOL's 11 and 11a is that the latter has a shoulder 29a and a projection 35a of somewhat different size and configuration. Specifically, the shoulder 29a is a sloping shoulder which is longer than the sloping shoulder 29, and it is formed by milling the peripheral wall 27a. Otherwise, the method of FIG. 6 is identical to the method of FIGS. 1-5.

FIGS. 7-9 show an IOL 11b which is identical to the IOL 11 in all respects not shown or described herein. Portions of the IOL 11b corresponding to portions of the IOL 11 are designated by corresponding reference numerals followed by the letter "b."

The only difference between the IOL's 11 and 11b is that the latter has internal screw threads which form the shoulder 29b in the bore 25b. The method of making the IOL 11b is the same as the method described in connection with FIGS. 1–5 for the IOL 11. Thus, an inner end portion of the fixation member 15b is inserted into the bore 25b as shown in FIG. 8 and heated through the material of the optic 13b with a laser (not shown) to cause at least some of the inner end portion of the fixation member 15b to flow to form a projection 35b in the form of external screw threads which interlock with the internal screw threads which form the shoulder 29b.

FIGS. 10–12 show an IOL 11c which is identical to the IOL 11 in all respects not shown or described herein. Portions of the IOL 11c corresponding to portions of the IOL 11 are designated by corresponding reference numerals followed by the letter "c."

With this invention, a hole 37 (FIG. 11) which may have a diameter of about 0.006 inch is drilled from the posterior face 21c of the optic 13c so as to intersect the bore 25c adjacent the inner end of the bore 25c. The surface of the hole 37 forms the shoulder 29c. In addition, laser energy from the laser 33c is transmitted through the optic 13c by being directed axially through the hole 37 to the inner end portion of the fixation member 15c as shown in FIG. 11. This melts a region of the inner end portion of the fixation member 15c to form a projection 35c as described above in connection with FIGS. 1–5 which interlocks with the shoulder 29c as shown in FIG. 12. Thus, this embodiment differs from the embodiment of FIGS. 1–5 in the formation of the shoulder 29c and in the transmission of laser energy through the hole 37 rather than through the material of the optic. Also, the bore 25c is not blind in that it communicates with the exterior through the hole 37.

Although exemplary embodiments of the invention have been shown and described, many changes, modifications and substitutions may be made by one having ordinary skill in the art without necessarily departing from the spirit and scope of this invention.

We claim:

1. A method of attaching a fixation member having an inner end portion to an optic of an intraocular lens wherein the optic has a peripheral edge, said method comprising:
   providing the optic with an outwardly opening cavity and with a shoulder within the cavity;
   inserting an inner end portion of the fixation member into the cavity;
   transmitting laser energy in the near infrared band through the optic to the inner end portion of the fixation member and absorbing the laser energy in said inner end portion sufficiently to heat the inner end portion to cause at least some of the inner end portion of the fixation member to flow behind the shoulder; and
   allowing the flowable portion of the fixation member to harden and interlock with the shoulder to resist withdrawal from the cavity.

2. A method as defined in claim 1 wherein said step of providing includes providing a bore which extends inwardly from adjacent the peripheral edge of the optic generally in the plane of the optic.

3. A method as defined in claim 2 wherein said step of providing includes providing the optic with a hole extending from the exterior of the optic to the cavity to thereby define at least a portion of said shoulder and said step of transmitting includes transmitting laser energy through said hole to the inner end portion of the fixation member.

4. A method as defined in claim 1 wherein said step of transmitting includes transmitting laser energy through the material of the optic to the inner end portion of the fixation member with the material of the optic and the inner end portion of the fixation member being sufficiently different so that the laser energy is transmitted by the optic without melting the optic and is absorbed by the inner end portion of the fixation member sufficiently to cause said flow.

5. A method as defined in claim 1 wherein said cavity has a peripheral wall and said step of providing includes drilling into said peripheral wall to at least partially define said shoulder.

6. A method as defined in claim 1 wherein said cavity has a peripheral wall and said step of providing includes providing a groove in said peripheral wall to at least partially define said shoulder.

7. A method as defined in claim 1 wherein said cavity has a peripheral wall and said step of providing includes tapping said cavity to provide screw threads in the peripheral wall to at least partially define said shoulder.

8. A method as defined in claim 1 wherein said cavity has a peripheral wall and said step of providing includes milling said shoulder in the peripheral wall.

9. A method as defined in claim 1 wherein said optic is constructed of PMMA and said laser energy has a wavelength of from about 1.06 to about 1.3 microns and said fixation member is constructed of a material other than PMMA.

10. A method as defined in claim 1 wherein said laser energy has a wavelength of from about 1.06 to about 1.3 microns.

11. A method as defined in claim 10 wherein the laser energy is provided by a Nd:YAG laser.

* * * * *